United States Patent
Takahashi et al.

(10) Patent No.: US 7,306,125 B2
(45) Date of Patent: Dec. 11, 2007

(54) DISPENSER FOR DENTAL VISCOUS MATERIAL

(75) Inventors: Masayuki Takahashi, Itabashi-ku (JP); Masaaki Kaneko, Itabashi-ku (JP); Kazuya Ishida, Nasu-Gun (JP)

(73) Assignee: GC Corporation, Tokyo (JP)

( * ) Notice: Subject to any disclaimer, the term of this patent is extended or adjusted under 35 U.S.C. 154(b) by 121 days.

(21) Appl. No.: 11/342,523

(22) Filed: Jan. 31, 2006

(65) Prior Publication Data

US 2006/0175356 A1 Aug. 10, 2006

(30) Foreign Application Priority Data

Feb. 8, 2005 (JP) ............... 2005-031884

(51) Int. Cl.
B67D 5/042 (2006.01)
B67B 5/00 (2006.01)

(52) U.S. Cl. ................. 222/391; 222/153.13

(58) Field of Classification Search ............. 222/391, 222/327, 153.13

See application file for complete search history.

(56) References Cited

U.S. PATENT DOCUMENTS 5,871,354 A 2/1999 Kunkel et al.
6,253,969 B1 * 7/2001 Nelson et al. ............ 222/391
6,296,484 B1 10/2001 Nihei et al.
6,439,439 B1 * 8/2002 Rickard et al. .......... 222/391

FOREIGN PATENT DOCUMENTS

| DE | 197 00 213 A1 | 7/1998 |
| JP | 2000-201951 | 7/2000 |
| JP | 2000-308647 | 11/2000 |
| JP | 2003-212278 | 7/2003 |

* cited by examiner

*Primary Examiner*—Kevin Shaver
*Assistant Examiner*—Melvin A. Cartagena
(74) *Attorney, Agent, or Firm*—Oblon, Spivak, McClelland, Maier & Neustadt, P.C.

(57) ABSTRACT

To prevent accidental discharge from a cartridge, a dispenser for the dental viscous material comprises a guide shaft 1 having a cylindrical part 1ba at a front end thereof, a guide member 1b having a large diameter part 1bba and a small diameter part 1bbb on the rear side of the cylindrical part 1ba, and a knob for rotating the guide shaft 1h at a rear end, a slide block 2 having a release plate 2c, and piston shafts 2b, a housing 3 having pressing springs 3ea, which press piston shafts 2b, and a lever main body 4 having a lever part 4a rotatable by a predetermined angle from a position in parallel to the housing 3 and a pressing piece 4b projected under the front side of the lever part 4a, to constitute a mechanism of switching of discharge state and discharge release state.

9 Claims, 7 Drawing Sheets

DISPENSER FOR DENTAL VISCOUS MATERIAL

BACKGROUND OF THE INVENTION

1. Field of the Invention

The present invention relates to a dispenser for a dental viscous material, which is capable of simultaneously discharging desired amounts of respective viscous materials from a cartridge, where two kinds of viscous materials for the dental viscous material are respectively stored.

2. Description of the Conventional Art

As for the dental viscous material comprising the two kinds of the viscous materials, since a chemical reaction is generally generated by mixing both viscous materials, the viscous materials are respectively stored in different containers in general. Thus, when using such a dental viscous material, it is used by measuring the necessary amount of each viscous material in each container (the amounts of the two kinds of viscous materials are equal in many cases), putting these viscous materials on a kneading paper or in a container for mixing, and mixing and kneading these materials by a rod, a spatula or the like.

However, as for such the dental viscous material, the chemical reaction is generally generated immediately after mixing these materials. Thus, it is necessary to carry out quickly a series of works for measuring the viscous materials and mixing and kneading those. More particularly, when the viscous materials are measured, for example, a tube must be used as the container for storing the viscous material, and a paper, in which a graduation line for measuring a length is preprinted, must be used as the kneading paper for mixing and kneading the two kinds of the viscous materials. Further, when the amounts of the viscous materials are equal, the tubes for storing these materials have same diameters of discharging ports, and each tube is pressed so as to discharge these materials with same lengths by referring to the graduation of the kneading paper, to thereby measure the viscous materials. Further, when the amounts of the viscous materials are not equal, the tubes having the different diameters of the discharging ports are used to discharge the viscous materials with the same lengths, or the tubes having the same diameters of the discharging ports are used to discharge these materials with the different lengths. Therefore, there are problems that the measuring work is troublesome and needs much time. Further, in addition to such a measuring work, an operator such as a dentist, an oral hygienist or the like, must carry out a work for mixing and kneading the viscous materials on the kneading paper, while taking care that these materials are fully mixed and bubbles are not immixed. Thus, there are problems that such the work needs not only certain skill but also large force at the time of mixing and kneading since the viscous material has high viscosity.

For solving such the problems, present inventors have developed a viscous material storing cartridge for storing the dental viscous material comprising the two kinds of viscous materials, and a dispenser for simultaneously discharging desired amounts of respective viscous materials from the viscous material storing cartridges.

As the viscous material storing cartridge for storing the dental viscous material comprising the two kinds of viscous materials, for example, following cartridge has been proposed (refer to Japanese Patent Application Laid Open No. 2000-201951). It is a viscous material storing cartridge comprising two parallel cylindrical bodies having opening parts at rear ends and discharging ports at front ends, and having constant cross-sectional shapes of the inner faces. In this cartridge, the rear ends is round flange parts formed in different shapes according to the stored material, the front ends are respectively connected with connecting parts, the dental viscous materials which are used by mixing with predetermined ratio are stored inside the cylindrical bodies, and opening parts of the rear ends are closed with caps for pushing out the stored materials. Further, a nozzle mounting part is provided at the front end of the cartridge to mount and hold a rear end of nozzle at the discharging port, and this nozzle is for dispensing the dental viscous materials pushed out from the insides of the cylindrical bodies while mixing and kneading those with a mixing tool. Further, the following cartridge also has been proposed (refer to Japanese Patent Application Laid Open No. 2003-212278). It is a viscous material storing cartridge comprising a viscous material storing part, a rotary shutter, a rotary shutter holding means, and a mixing tool mounting part. In this cartridge, the viscous material storing part comprises two parallel cylindrical bodies having opening parts at rear ends and discharging ports at front ends, and having constant cross-sectional shapes of the inner surfaces, and viscous material pushing out members are respectively fit to these inner faces. The rotary shutter has a size capable of closing at least all the discharging ports of the viscous material storing part, and has a communication hole provided at a position corresponding to the discharging ports. The rotary shutter holding means is provided at the front end of the viscous material storing part, and rotatably holds the rotary shutter, where the communication holes of the rotary shutter and the discharging ports of the viscous material storing part can be changed between a communicated state and a closed state by this shutter. The mixing tool mounting part is provided for mounting the mixing tool, which mixes the viscous materials in each cylindrical part discharged from the communication holes.

Further, as the dispenser for simultaneously discharging desired amounts of each viscous material from the viscous material storing cartridges, for example, the following dispenser has been proposed (refer to Japanese Patent Application Laid Open No. 2000-308647). It is a dispenser for a dental viscous material comprising a housing, a guide shaft, a lever, an elastic member, a slide block, a pressing spring, a piston shaft, and a braking member. In this dispenser, the housing has a cartridge mounting part at a front end, which is for mounting the cartridge storing the dental viscous material. The guide shaft is supported slidably in frontward and rearward directions in a cavity of the housing, and has a lever engaging part at a predetermined position. The lever is mounted freely on the housing by the lever shaft, where one end is engaged with the lever engaging part of the guide shaft and another end is positioned at the outside of the housing. The elastic member is provided for engaging the housing and the guide shaft with the lever in order to return the guide shaft to the initial position. The slide block has a space opening at the lower side therein and has an external shape in a box shape matching to the shape of the cavity of the housing. A through hole for inserting the guide shaft in the frontward and rearward directions is provided at the slide block. An adjusting screw is screwed at a position being lower than a penetration hole for the guide shaft at a front sidewall. The pressing spring is for forwardly pressing a release plate and provided between a rear side wall member of the slide block and the release plate. The release plate has a hole formed having a little larger size than the thickness of the guide shaft and matching the shape of guide shaft. The release plate is mountable in a state inclining to an axis of the guide shaft by adjusting a backwardly extending length of the adjusting screw. The guide shaft is inserted into the hole. The piston shaft is fixed to the slide block and has an axis which is parallel to the axis of the guide shaft for pressing the viscous material in the cartridge from the rear side. The braking member is provided in the housing, and constantly presses the piston shaft by the elastic force.

By using such the viscous material storing cartridge or the dispenser for the dental viscous material, when the needed amounts of respective viscous materials of the dental viscous materials are measured or the viscous materials are mixed and kneaded, the problems of the troublesome or taking much time are solved. Further, the problems that the skill is necessary and the large force at the time of mixing and kneading is needed since the viscous material has the high viscosity are solved. However, as for such the dispenser for the dental viscous material, the following problems remain unsolved. After discharging the desired amount of the viscous material, the dispenser for the dental viscous material is often put on a work table or kept in a refrigerator or a rack in the states that the viscous material storing cartridge having the residual viscous material is mounted on the cartridge mounting part and a top end of the piston shaft is contacted with the viscous material pushing out member of the viscous material storing cartridge. In such a state, the lever for forwardly transferring the guide shaft is pushed upwardly from the housing by the elastic member. Then, the lever is accidentally pressed downwardly, such that an object drops down from the upper side, a hand touches the lever during the dental treatment, or the lever is contacted with the rack or object when being kept in the refrigerator or the rack. Then, the trouble that the viscous material stored in the viscous material storing cartridge is discharged against will is caused.

Further, as for the slide block in which the piston shaft is fixed to press the viscous material pushing out member in the viscous material storing cartridge mounted on the cartridge mounting part, when an operation for pressing the lever is repeated, the slide block is gradually slid in the front direction in the cavity of the housing. In this case, by visually confirming the position of the slide block in the housing from the opening part at the lower part of the housing, a residual amount of the viscous material stored in the viscous material storing cartridge and an estimated amount of the viscous material discharged from the viscous material storing cartridge can be understood, so that it is convenient. However, when the lever is pressed, the opening part, from which the position of the slide block in the housing can be visually confirmed, is positioned at the lower side of the housing, so that, when pressing the lever actually, the opening part is hidden in a palm. Thus, in order to confirm the position of the slide block in the housing, an operator pressing the lever must once stop the work specially to reverse the housing by 180 degrees. Therefore, there is a problem that such operator pressing the lever cannot carry out the work in actuality while confirming the residual amount or the discharged amount of the viscous material.

Furthermore, when the viscous material storing cartridge mounted on the cartridge mounting part is removed after discharging the desired amount of the viscous material, the release plate is pressed against the pressing spring provided between the rear side wall member and the release plate, and the slide block is backwardly pressed while keeping the release plate perpendicular the axis of to the guide shaft, to thereby slide the piston shaft to the initial position, where the release plate is mountable in the inclining state with respect to the axis of the guide shaft. Then, the viscous material storing cartridge is removed from the cartridge mounting part. However, since the release plate and the slide block are positioned at the lower part of the housing, the housing must be reversed by 180 degrees when carrying out such the operation. Thus, there is a problem for actually operating it.

SUMMARY OF THE INVENTION

The present invention solves the above-described problems of the conventional techniques, and an objective of the present invention is to provide the dispenser for the dental viscous material capable of simultaneously discharging the desired amounts of respective viscous materials from the cartridge, where the two kinds of viscous materials for the dental viscous material are respectively stored. More particularly, it is, the dispenser for the dental viscous material, in which discharging of the viscous material against will is prevented, when not necessary to discharge the viscous material, and the operativity is enhanced.

The earnest work was carried out in order to solve the above-mentioned problems and, as a result of this, the followings were found to complete the present invention. The dispenser has the mechanism, in which a lever main body can be transferred from an initial position where a pressing force for sliding a guide shaft in the front direction cannot be transmitted, to a position where the pressing force can be transmitted, by rotating the guide shaft which is supported rotatably and slidably in axial direction in a housing. The lever part of the lever main body is approximately in parallel to an upper face of a housing at the initial position and rotated upwardly by the predetermined angles at the position where the pressing force can be transmitted. Further, the dispenser also has the structure, in which the slide block can be operated and the position thereof can be confirmed from upper side of the housing. Then, it can be prevented to discharge the viscous material against will, and the operativity can be enhanced.

That is, the present invention is a dispenser for the dental viscous material comprising a guide shaft, a slide block, a housing, and a lever main body.

The guide shaft comprises a guide member mounting part, a guide member, a first stopper ring engaging groove, a first stopper ring, a rotation knob mounting part, a second stopper ring engaging groove, a second stopper ring, a spring, and a knob for rotating the guide shaft. The guide member comprises a cylindrical part at a front side of the guide member mounting part formed at a front end of the guide shaft, and a guide part at a rear side of the guide member mounting part. The guide part comprises a large diameter part and a small diameter part increasing the diameter toward a rear side. The first stopper ring is engaged with the first stopper ring engaging groove, which is formed at the rear side of the guide member mounting part. The second stopper ring is engaged with the second stopper ring engaging groove of the rotation knob mounting part, which is formed at a rear end of the guide shaft. The knob for rotating the guide shaft is freely fit to a non-circle part formed at a rear side of the second stopper ring engaging groove, and is constantly given the sliding force in the front direction of the shaft by the spring, which is provided at a space between the second stopper ring and a front end part of the knob. At least a portion between the rear side of the first stopper ring engaging groove and the front side of the rotation knob mounting part has a pillar shape.

The slide block comprises a box shaped-block part, rod-like piston shafts, a release plate, and a release plate pressing spring. The box shaped-slide block part has a hole for the guide shaft, in which the guide shaft is inserted freely and movably. The hole for the guide shaft is provided at a front side wall part to a rear side wall part, where a projecting plate having a projected release plate supporting part on a rear face is upwardly projected at the front side wall part. Further, at least the upper face of the block part is opened. The rod-like piston shafts are projected at positions on the both sides of the hole for the guide shaft at the front side wall part of the block part, where axes of the shafts are in approximately parallel to a center axis of the hole for the guide shaft. The release plate has an engaging hole for the guide in the space of the block part in which the portion of the guide shaft between the first stopper ring engaging groove and the rotation knob mounting part is inserted into this engaging hole for the guide, and a distance from the upper end to the lower end of this engaging hole is longer than the diameter of this position. Further, as for the release plate, the upper side of the front face is contacted with the rear face of the release plate supporting part of the projecting plate. The release plate pressing spring presses the release plate in the front direction in the space of the block part so as to contact the upper end and the lower end of the engaging hole for the guide to the guide shaft.

The housing comprises a cartridge mounting part, a guide member supporting part, a first guide shaft supporting part, a guide member pressing chamber, a second guide shaft supporting part, a slide block moving chamber, one pair of a piston shaft guiding passage, one pair of a piston shaft pressing spring chamber, and a lever mounting part. The cartridge mounting part is provided at a front end of the housing, and is for mounting the cartridge storing the dental viscous material. The guide member supporting part is provided at a rear side of the cartridge mounting part, and is for constantly supporting the cylindrical part of the guide member, where the cylindrical part is supported rotatably and silidably in the axial direction. The first guide shaft supporting part supports the portion between the first stopper ring engaging groove of the guide shaft and the rotation knob mounting part, where this portion is supported rotatably and silidably in the axial direction. The guide member pressing chamber is provided between the guide member supporting part and the first guide shaft supporting part, has an opening at upper part, and has a space in which a guide part of the guide member can be rotated and moved. The second guide shaft supporting part is provided at a rear side of the first guide shaft supporting part, and supports a portion between the first stopper ring engaging groove of the guide shaft and the rotation knob mounting part at a rear end wall of the housing, where this portion is supported rotatably and slidably in the axial direction. The slide block moving chamber has an opening at upper part to approximately full length. The one pair of the piston shaft guide passages are provided on the both sides of the guide member pressing chamber, supports the piston shafts of the slide block slidably in the axial direction, and penetrate from the slide block moving chamber to the cartridge mounting part. The one pair of the piston shaft pressing spring chambers are formed for providing piston shaft pressing spring so as to contact one side ends of these springs with the respective each piston shafts in the piston shaft guide passages. The lever mounting part is provided at the upper part of the guide member pressing chamber.

The lever main body comprises a lever part and a pressing piece. The lever part is provided at the lever mounting part of the housing, and axially supported by a lever shaft so as to be rotated from at least the position being approximately parallel to the upper face of the housing to a position where a rear part thereof has predetermined angles with respect to the upper face of the housing. The pressing piece is moved to a rear part by a stepped part at a boundary between a small diameter part and a large diameter part of the guide part, by inserting the lever part into a small diameter part of the guide part and rotating the knob for rotating the guide shaft in the initial position being approximately parallel to the upper face of the housing. Then, the pressing piece rotates the lever part upwardly by predetermined angles, and is contacted with a rear face of the large diameter part of the guide part. This pressing piece is projected at a lower part on the front end side of the lever part. When a rear end of the lever part is pressed to the housing side, the pressing piece moves the rear face of the large diameter part of the guide part in the front direction.

Further, the followings were also found out. A stopper having a projected part projected downwardly is movably provided at the lever part of the lever main body, and a recessed part is formed at a position corresponding to the projected part, where the recessed part position is on the upper face side of the housing when the stopper is positioned on the most rear side. In such a structure, when the rear end of the lever part is pressed on the housing side, a stroke of the piston shaft sliding in the front direction can be adjusted. So, it is preferable. Further, the lever part of the lever main body is formed to have a U-shaped cross section, where a lower part is opened, so that it can cover the projecting plate and the release plate. The projecting plate is projected from the slide block moving chamber of the housing. Further, the lever part of the lever main body is in parallel to the guide shaft in the initial position, and can be rotated from the initial position to a position which is approximately vertical to the guide shaft. In such a structure, the dispenser can be more miniaturized when keeping the dispenser for the dental viscous material according to the present invention. So, it is preferable.

Further, a projected part and a recessed part are formed at the front face of the knob for rotating the guide shaft and the rear end outer face of the housing, and these parts are engaged each other when the guide part is rotated to a predetermined position by the knob. Further, a guide shaft pressing spring is provide on the front side of the guide member supporting part of the housing and gives the force for constantly pressing the front end of the cylindrical part of the guide member in the rear direction. Then, the operativity is more enhanced, so that it is preferable.

The dispenser for the dental viscous material according to the present invention has the above-described constitutions. Thus, by rotating the knob for rotating the guide shaft, which is mounted on the rear end of the guide shaft supported rotatably and slidably in the axial direction in the housing and mounted at the rear end of the guide shaft, the following two states can be freely changed. One state is that the lever part of the lever main body can be rotated from the initial position to the position where the rear part of the lever part has the predetermined angle with respect to the upper face of the housing, where the initial position is approximately in parallel to the upper face of the housing and the viscous material stored in the cartridge mounted on the cartridge mounting part of the housing can not be discharged (hereinafter, it is called as a discharge release state). Another state is that the lever part is positioned at the upper part having the predetermined angles to the initial position and the viscous material stored in the cartridge can be discharged when the rear end of the lever part is pressed on the housing side (hereinafter, it is called as a discharge possible state). Thus, there are the following advantage, when the dispenser for the dental viscous material according to the present invention is put on the work table or the like or kept in the refrigerator or the rack after discharging the viscous material stored in the cartridge, in a state that the viscous material storing cartridge having a remained viscous material is mounted on the cartridge mounting part, and the top end of the piston shaft is contacted with the viscous material pushing out member of the viscous material storing cartridge. The advantage is that, only by rotating the knob for rotating the guide shaft to change to the discharge release state, the trouble that the viscous material stored in the cartridge is discharged against will is not generated at all even when the lever part of the lever main body is compulsorily rotated. Further, the lever part is positioned at the initial position being in approximately parallel to the upper face of the housing. Thus, since the lever does not become obstructive when keeping the dispenser, the keeping space of the dispenser can be remarkably small as compared with that of the conventional dispenser for the dental viscous material. Furthermore, there is a following advantage when the dental viscous material according to the present invention is used again after putting it on the work table or the like or keeping it in the refrigerator or the rack in the state that the viscous material storing cartridge having the remained viscous material is mounted on the cartridge mounting part, and the top end of the piston shaft is contacted with the viscous material pushing out member of the viscous material storing cartridge. The advantage is that, only by rotating the knob for rotating the guide shaft to change from the discharge release state to the discharge possible state, the viscous material stored in the cartridge can be discharged immediately. Thus, the operativity and the convenience can be remarkably increased.

That is, as for the dispenser for the dental viscous material according to the present invention, the guide member fixed at the front end of the guide shaft has the guide part comprising the large diameter part in the rear side and the small diameter part increasing the diameter toward the rear side, where the guide shaft is supported in the housing rotatably and slidably in the axial direction. Thus, when the small diameter part of the guide part of the guide member is at a position directing upwardly, the pressing piece projected at the lower part of the lever part of the lever main body is in the state of being inserted into the small diameter part without contacting with the guide part of the guide member. Thus, the lever part of the lever main body can be freely rotated from the initial position being in approximately parallel to the upper face of the housing to the position where the rear part of the lever part has the predetermined angles with respect to the upper face of the housing. Further, the pressing piece of the lever main body cannot give the pressing force to the guide part of the guide member. Thus, even when the lever part of the lever main body is rotated to be transferred to the position being in approximately parallel to the upper face of the housing, the guide shaft and the piston shaft are not slid in the front direction, so that the dispenser becomes in the discharge release state where the dental viscous material stored in the cartridge cannot be discharged. On the other hand, when the guide shaft is rotated by the knob for rotating the guide shaft, and the large diameter part of the guide part is transferred to the position where the large diameter part is directed upwardly from the discharge release state, the pressing piece of the lever main body is moved in the rear direction by the stepped part of the boundary between the small diameter part and the large diameter part of the guide part. Then, the lever part is rotated from the initial position being in approximately parallel to the upper face of the housing to the position where the rear part of the lever part has the predetermined angles with respect to the upper face of the housing. Simultaneously, the pressing piece is transferred to the state of being contacted with the rear face of the large diameter part of the guide part. Therefore, the dispenser becomes in the discharge possible state where the viscous material stored in the cartridge can be discharged when the rear end of the lever part is pressed on the housing side.

Further, the housing has the slide block moving chamber where the upper part is opened to approximately full length. Thus, when the position of the slide block in the slide block moving chamber is viewed in order to confirm a residual amount of the viscous material stored in the viscous material storing cartridge and an estimated discharged amount of the viscous material from the viscous material storing cartridge, the position of the slide block can be easily confirmed from the upper side without once stopping the operation for pressing the lever. Further, when the viscous material storing cartridge mounted on the cartridge mounting part is removed after discharging the desired amount of the viscous material, the cartridge can be removed from the cartridge mounting part only by pressing the slide block in the rear direction while pressing the release plate in the front direction from the upper side, and thereby sliding the piston shaft to the initial position. Thus, it is not necessary to reverse the housing by 180 degrees like the conventional dispenser for the dental viscous material, so that the operativity can be remarkably enhanced.

Further, the stopper having the projected part projected downwardly is movably provided at the lever part of the lever main body, and the recessed part is formed at the position corresponding to the projected part, where the position of the recessed part is on the upper face side of the housing, when the stopper is positioned on the most rear side. Then, since the rotation angle of the lever part can be controlled by moving the stopper frontward and rearward, the stroke of the piston shaft when the rear end of the lever part is pressed on the housing side can be adjusted. Thus, the discharging amount of the viscous material can be changed, so that it is preferable. Further, when the dispenser for the dental viscous material according to the present invention is kept, the stopper is moved to the position on the most rear side, to thereby insert the projected part of the stopper into the recessed part of the upper face of the housing, and to thereby position the lever part in approximately parallel to the upper face of the housing. Thus, a space at the time of keeping is small, so that it is preferable.

Further, the lever part of the lever main body is formed to have the U-shaped cross section where the lower part is opened, and this part is formed so as to cover the projecting plate and the release plate, where the projecting plate is projected from the slide block moving chamber of the housing. Then, when the dispenser for the dental viscous material according to the present invention is kept, the dispenser can be more miniaturized, so that it is preferable. Further, when the lever part is in the initial position being in approximately parallel to the upper face of the housing, the slide block moving chamber of the housing is covered with the lever part. Thus, when the dispenser is kept, it can be prevented that dust, extraneous substance or the like is invaded to damage the operativity of the dispenser or the dispenser itself. So, it is preferable. Further, in such a state, since the inside of the housing cannot be seen from the outside, it gives better appearance, so that it is preferable.

Further, the lever part of the lever main body can be rotated from the initial position being in parallel to the guide shaft to the position being in approximately perpendicular to the guide shaft. Then, when the dispenser for the dental viscous material according to the present invention is kept, the dispenser can be more miniaturized as compared with that in use. So, it is preferable. Furthermore, when the lever part is rotated to the position being in approximately perpendicular to the guide shaft, it is easy to carry out, the operation for pressing the slide block in the rear direction while pressing the release plate in the front direction, to thereby slide the piston shaft to the initial position. So, it is preferable.

Furthermore, the projected part and the recessed part are formed at the front face of the knob for rotating the guide shaft and the rear end outer face of the housing, where the projected part and the recessed part are engaged each other when the guide part is rotated to the predetermined position by the knob for rotating the guide shaft. Then, the discharge release state and the discharge possible state can be certainly changed. Thus, the operativity of the knob for rotating the guide shaft can be enhanced, so that it is preferable. Further, the guide shaft pressing spring is provided on the front side of the guide member supporting part of the housing, where the spring gives the force for constantly pressing the front end of the cylindrical part in the rear direction. Then, the rear end side of the guide shaft is constantly pressed in the rear direction by the spring provided at the knob for rotating the guide shaft, and the front end side thereof is constantly pressed in the rear direction by the guide shaft pressing spring. Thus, the guide shaft and the lever part can be certainly moved, so that it is preferable. Further, it can be prevented to damage the guide member or the housing by violently crashing the front end of the large diameter part of the guide member to the front end of the guide member pressing chamber of the housing.

DETAILED DESCRIPTION OF PREFERRED EMBODIMENT

Hereinafter, the dispenser for the dental viscous material according to the present invention is explained concretely with drawings.

Figure 1:
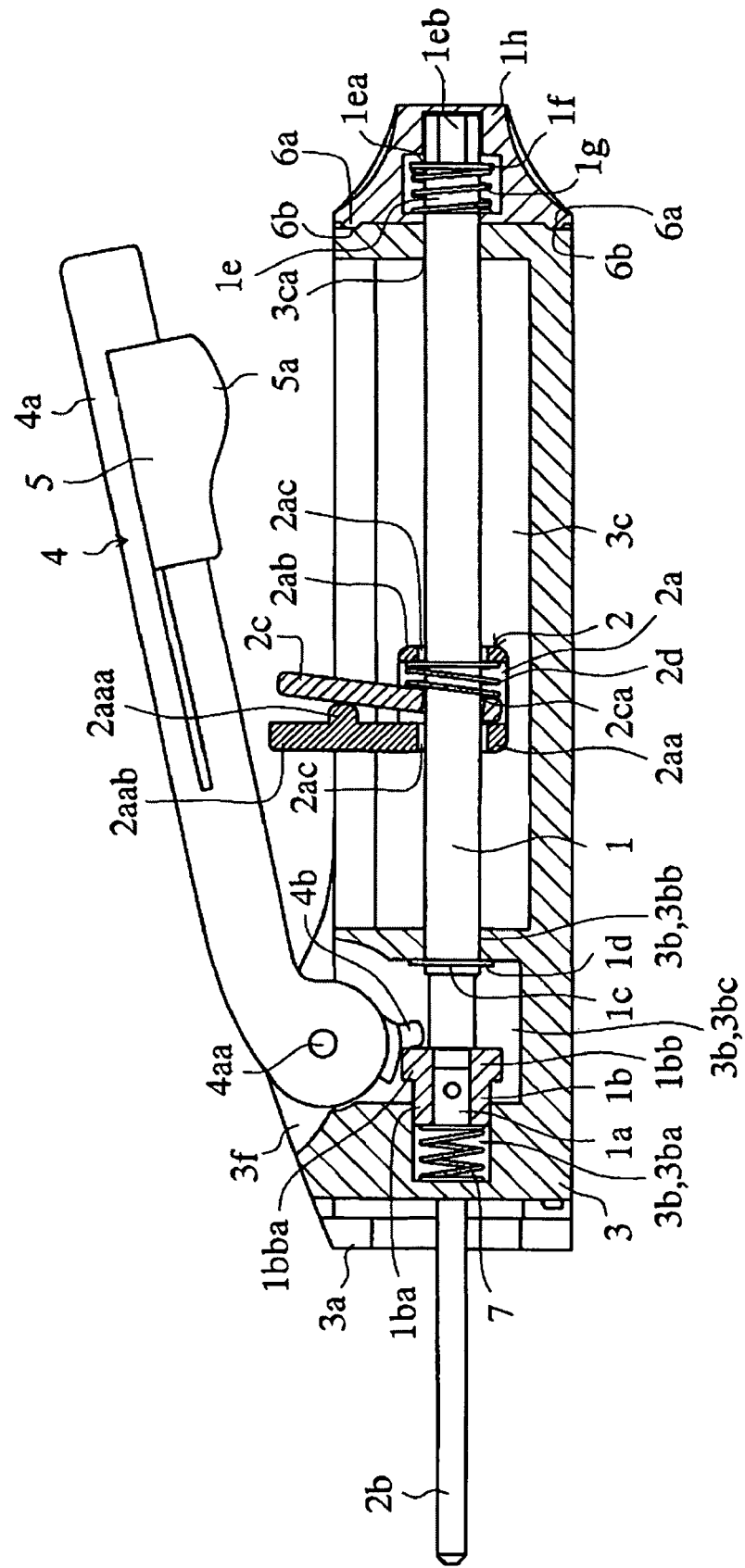
FIG. 1 is a side cross-sectional explanation view illustrating one example of a dispenser for a dental viscous material according to the present invention, in a state that the dispenser is cut longitudinally in the center and a lever main body is not cut.
Figure 2:
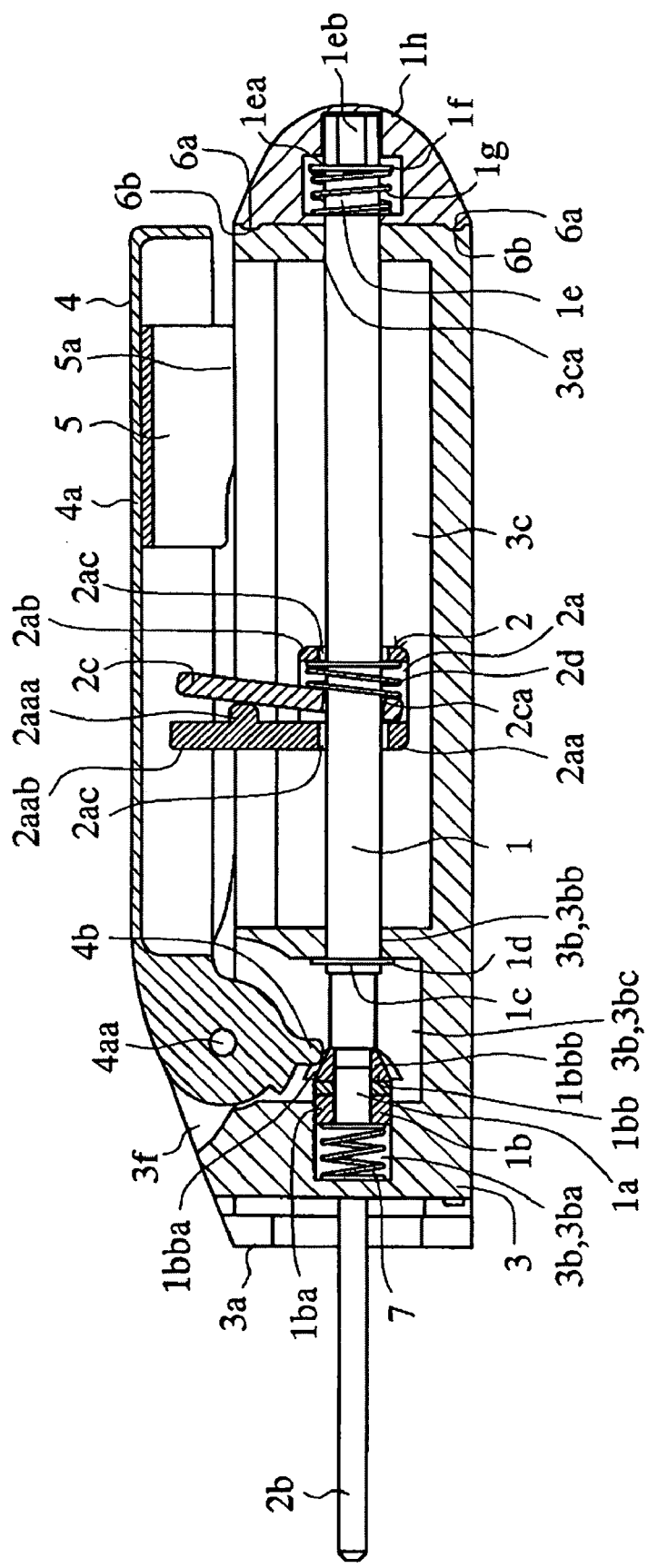
FIG. 2 is a side cross-sectional explanation view illustrating a positional relationship of a guide member, a lever part and a slide block, in a state that the lever part of the dispenser for the dental viscous material of FIG. 1 is in the initial position and the guide member is in the position of a discharge release state.
Figure 3:
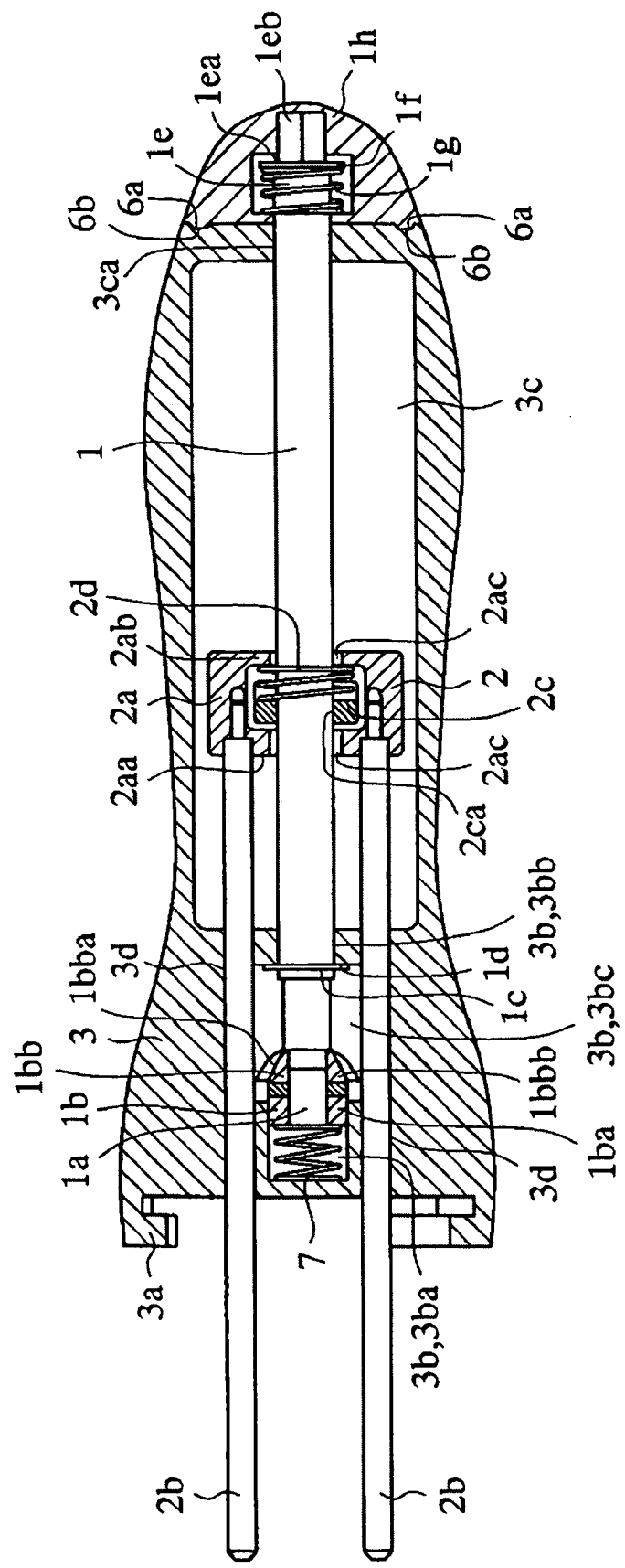
FIG. 3 is a plan cross-sectional explanation view of FIG. 1.
Figure 4:
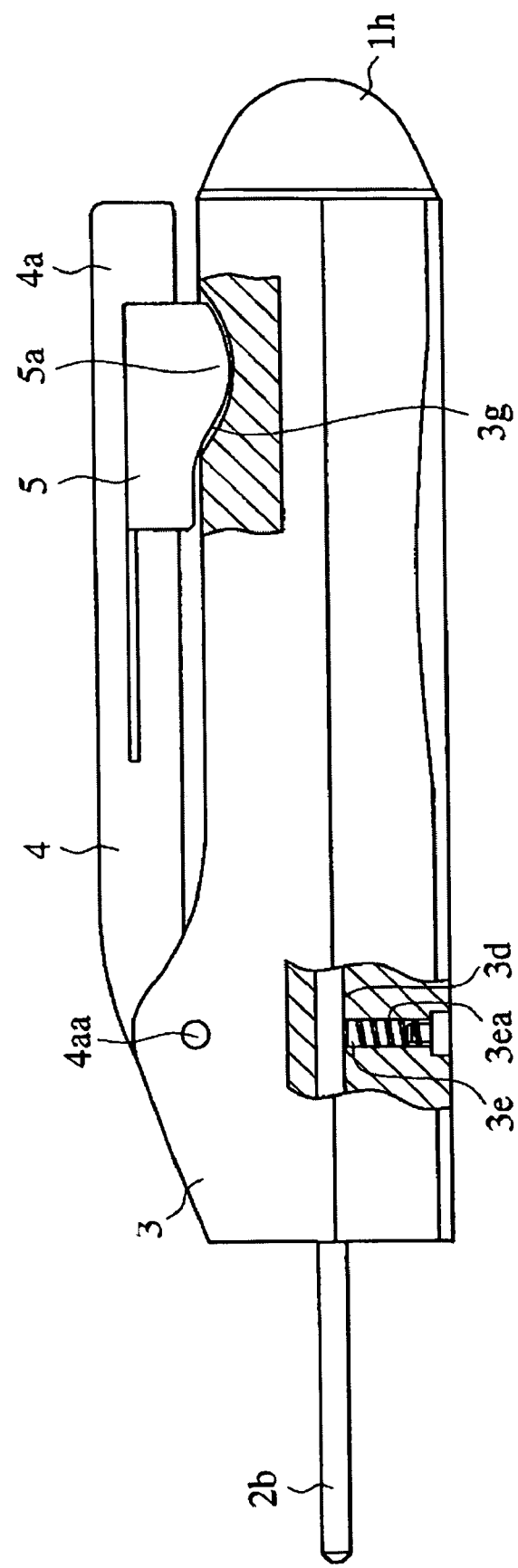
FIG. 4 is a side explanation view illustrating cross sections around a piston shaft pressing spring chamber and a stopper of the dispenser for the dental viscous material of FIG. 2.
Figure 5:
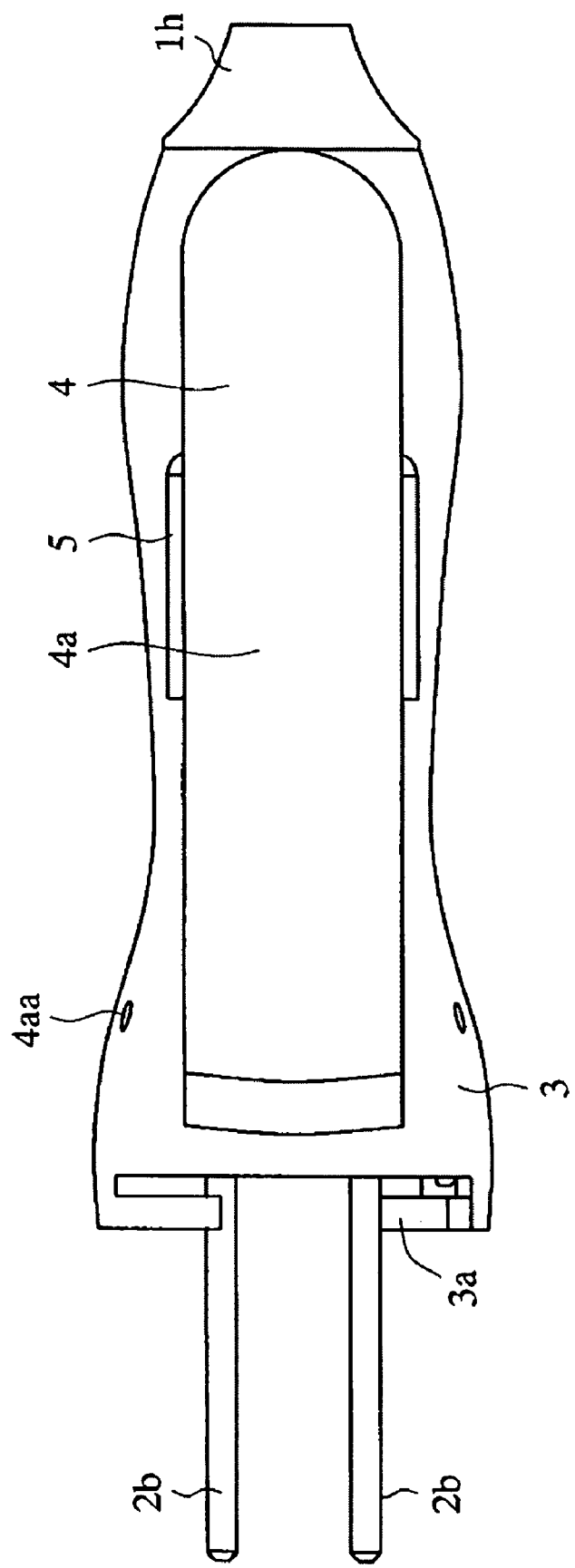
FIG. 5 is a plan view of FIG. 2.
Figure 6:
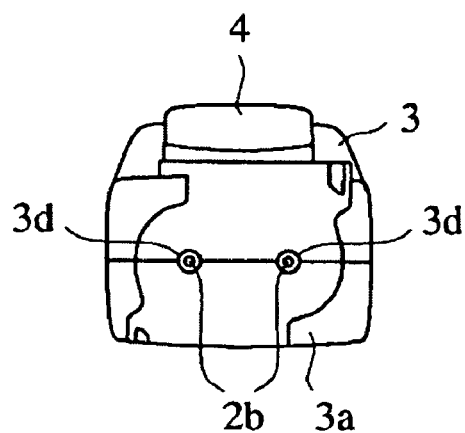
FIG. 6 is a front view of FIG. 2.
Figure 7:
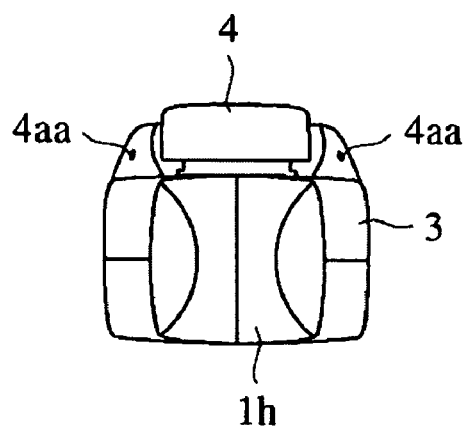
FIG. 7 is a rear view of FIG. 2.
Figure 8:
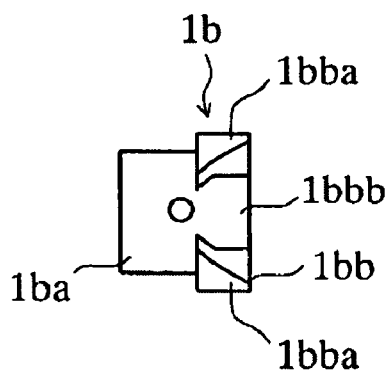
FIG. 8 is an enlarged side view illustrating one example of the guide member.
Figure 9:
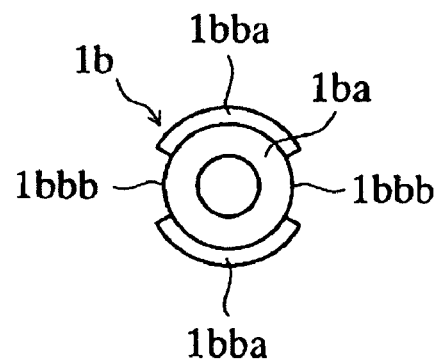
FIG. 9 is a front view of FIG. 8.
Figure 10:
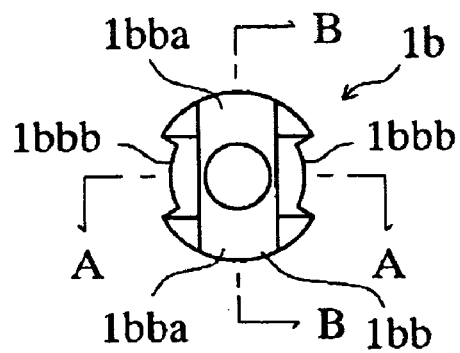
FIG. 10 is a rear view of FIG. 8.
Figure 11:
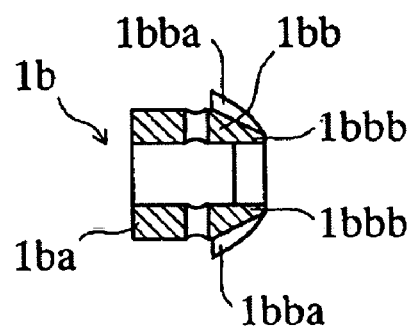
FIG. 11 is a cross-sectional view taken along a line A-A of FIG. 10.
Figure 12:
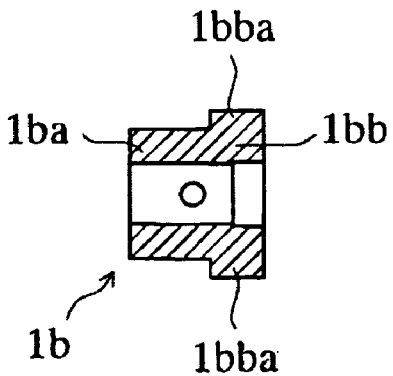
FIG. 12 is a cross-sectional view taken along a line B-B of FIG. 10.

FIG. 1 is a side cross-sectional explanation view illustrating one example of a dispenser for a dental viscous material according to the present invention, in a state that the dispenser is cut longitudinally in the center and a lever main body is not cut. FIG. 2 is a side cross-sectional explanation view illustrating a positional relationship of a guide member, a lever part and a slide block, in a state that the lever part of the dispenser for the dental viscous material of FIG. 1 is in the initial position and the guide member is in the position of a discharge release state. FIG. 3 is a plan cross-sectional explanation view of FIG. 1. FIG. 4 is a side explanation view illustrating cross sections around a piston shaft pressing spring chamber and a stopper of the dispenser for the dental viscous material of FIG. 2. FIG. 5 is a plan view of FIG. 2. FIG. 6 is a front view of FIG. 2. FIG. 7 is a rear view of FIG. 2. FIG. 8 is an enlarged side view illustrating one example of the guide member. FIG. 9 is a front view of FIG. 8. FIG. 10 is a rear view of FIG. 8. FIG. 11 is a cross-sectional view taken along a line A-A of FIG. 10. FIG. 12 is a cross-sectional view taken along a line B-B of FIG. 10.

In the drawings, reference numeral 1 is a guide shaft. The guide shaft 1 comprises a guide member mounting part 1a, a guide member 1b, a first stopper ring engaging groove 1c, a first stopper ring 1d, a rotation knob mounting part 1e, a second ring stopper 1f, a spring 1g, and a knob for rotating the guide shaft 1h. In this guide shaft 1, the guide member 1b has a cylindrical part 1ba at a front side of the guide member mounting part 1a formed at a front end of the guide shaft 1, and a guide part 1bb at a rear side of the guide member mounting part 1a, where the guide part 1bb comprises a large diameter part 1bba and a small diameter part 1bbb increasing the diameter toward the rear side. The first stopper ring 1d is engaged with the first stopper ring engaging groove 1c, which is formed at the rear side of the guide member mounting part 1a. The second stopper ring 1f is engaged with the second stopper ring engaging groove 1ea of the rotation knob mounting part 1e, which is formed at a rear end of the guide shaft 1. The knob for rotating the guide shaft 1h is freely fit to a non-circle part 1eb formed at a rear side of the second stopper ring engaging groove 1ea, and is constantly given the force for sliding in the front direction of the shaft by the spring 1g. The spring 1g is provided at a space between the second stopper ring 1f and a front end part of the knob 1h. At least a portion between the rear side of the first stopper ring engaging groove 1c and the front side of the rotation knob mounting part 1e has a pillar shape. When the guide shaft 1 is moved in the front direction by a lever main body 4 described below, it performs function to move a piston shaft 2b of a slide block 2 described below in the front direction.

The guide shaft 1 has the guide member mounting part 1a formed at the front end thereof for fixing the guide member 1b. As the guide member mounting part 1a, a part for fixing the guide member 1b with a pin may be used as illustrated in FIGS. 1 to 3, or a part for pressing-in the guide member 1b or fixing it with a key groove and a key may be used although it is not illustrated in the drawings.

The guide member 1b fixed at the guide member mounting part 1a in the front end of the guide shaft 1 comprises the cylindrical part 1ba at a front side thereof and the guide part 1bb at the rear side thereof. The guide part 1bb comprises the large diameter part 1*bba* and the small diameter part 1*bbb* increasing the diameter toward the rear side, as illustrated in FIGS. 8 to 12. This guide member 1*b* transmits the pressing force to the guide shaft 1, where the pressing force is for moving the guide shaft 1 in the front direction by the lever main body 4 described below. Further, the guide member 1*b* performs function to change the discharge release state and the discharge possible state of the dispenser for the dental viscous material according to the present invention, by rotating the knob for rotating the guide shaft 1*h* mounted on the rotation knob mounting part 1*e*, which is formed at the rear end of the guide shaft 1.

As for the guide part 1*bb* of the guide member 1*b*, when the small diameter part 1*bbb* of the guide part 1*bb* is directed upwardly as illustrated in FIG. 2, the pressing piece 4*b* of the lever main body 4 described below is inserted into the small diameter part 1*bbb* without contacting with the guide part 1*bb*. Thus, the lever part 4*a* of the lever main body 4 can be freely rotated from the initial position, which is in approximately parallel to the upper face of the housing 3 described below, to the position where the rear part thereof has the predetermined angles with respect to the upper face of the housing 3. Further, even when the lever part 4*a* of the lever main body 4 is rotated to transfer to the position being in approximately parallel to the upper face of the housing 3, the guide shaft 1 cannot be moved in the front direction. Further, when the guide shaft 1 is rotated by the knob for rotating the guide shaft 1*h* to transfer from the above described state to the state where the large diameter part 1*bba* of the guide part 1*bb* is directed upwardly as illustrated in FIG. 1, the pressing piece 4*b* of the lever main body 4 is moved in the rear direction by the stepped part of the boundary between the small diameter part 1*bbb* and the large diameter part 1*bba* of the guide part 1*bb* as illustrated in FIGS. 8 to 11. Then, the lever part 4*a* is rotated from the initial position being in approximately parallel to the upper face of the housing 3 to the position where the rear end thereof has the predetermined angles with respect to the upper face of the housing 3, and the pressing piece 4*b* is moved on the rear face side of the large diameter part 1*bba* of the guide part 1*bb*. Thus, when the rear end of the lever part 4*a* is pressed on the housing 3 side, the lever part 4*a* is rotated, and then, the pressing piece 4*b* presses the rear face of the large diameter part 1*bba* of the guide part 1*bb*, to thereby move the guide shaft 1 in the front direction.

The rear part of the guide member mounting part 1*a* of the guide shaft 1 has the first stopper ring engaging groove 1*c*, which is formed for engaging the first stopper ring 1*d*, as illustrated in FIGS. 1 to 3. By impacting to a rear end wall of a space 3*bc* of a guide member pressing chamber 3*b* of the housing 3 described below, the first stopper ring 1*d* controls the stroke for sliding in the rear direction of the guide shaft 1, which is constantly pressed in the rear direction by the spring 1*g* provided at the space of the knob for rotating the guide shaft 1*h* and, preferably, the guide shaft pressing spring 7 described below. Further, the first stopper ring 1*d* prevents to remove the guide shaft 1 from the rear end of the housing 3.

The rear end of the guide shaft 1 has the rotation knob mounting part 1*e* comprising the second stopper ring engaging groove 1*ea* and the non-circle part 1*eb* formed at the rear side of the second stopper ring engaging groove 1*ea*, as illustrated in FIGS. 1 to 3. The rotation knob mounting part 1*e* has the knob for rotating the guide shaft 1*h*, which is mounted for rotating the guide shaft 1 around its axis, as illustrated in FIGS. 1 to 5 and 7.

The knob for rotating the guide shaft 1*h* is freely fit to the non-circle part 1*eb* of the rotation knob mounting part 1*e*, as illustrated in FIGS. 1 to 3. (The non-circle part 1*eb* is a right hexagonal column in FIG. 1 to 3.) Further, the knob 1*h* is mounted on the rotation knob mounting part 1*e* in the state of being constantly given the force for sliding in the front direction of the shaft by the spring 1*g*, which is provided at the space between the second stopper ring 1*f* and the front end part of the knob for rotating the guide shaft 1*h*. The second stopper ring 1*f* is engaged with the second stopper ring engaging groove 1*ea* of the rotation knob mounting part 1*e*. Since the knob for rotating the guide shaft 1*h* is freely fit to the non-circle part 1*eb* of the rotation knob mounting part 1*e*, the guide shaft 1 can be rotated around its axis. Further, since the spring 1*g*, which constantly gives the force for sliding in the front direction of the shaft, is provided at the space between the second stopper ring 1*f* and the front end part of the knob for rotating the guide shaft 1*h*, the force is given for pressing the front face of the knob for rotating the guide shaft 1*h* to a rear end outer face of the housing 3 described below. Thus, it can be prevented to remove the knob for rotating the guide shaft 1*h* from the guide shaft 1, and the force for sliding in the rear direction can be given with respect to the guide shaft 1.

Further, as illustrated in FIGS. 1 to 3, the projected part 6*a* and the recessed part 6*b* are formed at the front face of the knob for rotating the guide shaft 1*h* and the rear end outer face of the housing 3 described below, where these parts 6*a* and 6*b* are engaged each other when the guide part 1*bb* is rotated to the predetermined position by the knob for rotating the guide shaft 1*h*. Then, since the discharge release state and the discharge possible state can be certainly changed, the operativity of the knob for rotating the guide shaft can be enhanced so that it is preferable.

At this time, the knob for rotating the guide shaft 1*h* has the spring 1*g* constantly giving the force for sliding in the shaft front direction, and this spring 1*g* is provided at the space between the second stopper ring 1*f* and the front end part of the knob for rotating the guide shaft 1*h*, so that the knob for rotating the guide shaft 1*h* is given the force for pressing the front face thereof to the rear end outer face of the housing 3 described below. Thus, when the knob for rotating the guide shaft 1*h* is positioned in the discharge release state as illustrated in FIG. 2 or in the discharge possible state as illustrated in FIG. 1, the projected part 6*a* and the recessed part 6*b* are in the state of being engaged each other. Further, in the case that the discharge release state is changed to the discharge possible state or the discharge possible state is changed to the discharge release state, when the knob for rotating the guide shaft 1*h* is rotated, the engaging of the projected part 6*a* and the recessed part 6*b* is separated, and the knob for rotating the guide shaft 1*h* is moved in the rear direction against the force of the spring 1*g* only by the height of the projected part 6*a*, to thereby contact a top part of the projected part 6*a* with the front face of the knob for rotating the guide shaft 1*h* or the rear end outer face of the housing 3. Thereafter, when the knob for rotating the guide shaft 1*h* is moved to the discharge release state or the discharge possible state, the projected part 6*a* and the recessed part 6*b* are in the state of being engaged each other again by the force of the spring 1*g*. Thus, only by sense of a finger when rotating the knob for rotating the guide shaft 1*h*, it can be judged whether the knob for rotating the guide shaft 1*h* is exactly positioned in the discharge release state or the discharge possible state. The effects of the projected part 6*a* and the recessed part 6*b* are not changed whether they are provided either side of the front face of the knob for rotating the guide shaft 1h and the rear end outer face of the housing 3 respectively or vice versa.

Such a guide shaft 1 has a pillar-shaped portion at least between the rear part of the first stopper ring engaging groove 1c and the front part of the rotation knob mounting part 1e, as illustrated in FIGS. 1 to 3. Further, this portion has the movably mounted slide block 2 described below, and is supported rotatably and slidably in the axial direction by the first guide shaft supporting part 3bb and the second guide shaft supporting part 3ca of the housing 3 described below.

Reference numeral 2 is a slide block provided movably on a portion between the first stopper ring engaging groove 1c and the rotation knob mounting part 1e. The slide block 2 comprises a box-shaped block part 2a, rod-like piston shafts 2b, 2b, a release plate 2c, and a release plate pressing spring 2d. The box shaped-slide block part 2a has a hole for the guide shaft 2ac, in which the guide shaft 1 is inserted movably in this hole 2ac which is provided at a front side wall part 2aa to a rear side wall part 2ab. A projecting plate 2aab having a projected release plate supporting part 2aaa on a rear face is upwardly projected on the front side wall part 2aa. Further, as for the box-shaped block part 2a, at least the upper face is opened. The rod-like piston shafts 2b, 2b are projected at positions on the both sides of the hole for the guide shaft 2ac of the front side wall part 2aa of the block part 2a, in the state that axes of the shafts are in approximately parallel to a center axis of the hole for the guide shaft 2ac. The release plate 2c is provided in a space of the block part 2a and has an engaging hole for the guide 2ca in which the portion between the first stopper ring engaging groove 1c of the guide shaft 1 and the rotation knob mounting part 1e is inserted into this hole 2ca. The engaging hole for the guide 2ca is formed in the block part 2a to have a longer distance from the upper end to the lower end of the engaging hole 2ca than the diameter of the portion of the guide shaft 1. Further, the front face of the upper part of the release plate 2c is contacted with the rear face of the release plate supporting part 2aaa of the projecting plate 2aab. The release plate pressing spring 2d presses the release plate 2c in the front direction so as to contact the upper end and the lower end of the engaging hole for the guide 2ca to the guide shaft 1 in the space of the block part 2a. The slide block 2 is moved intermittently in the front direction in the housing 3 described below by the guide shaft 1, to thereby press the cap for pushing out the stored material of the cartridge by the one pair of the piston shafts 2b, 2b, and to thereby discharge the viscous material from the cartridge.

As illustrated in FIGS. 1 to 3, the box shaped-block part 2a in the slide block 2 having the opening upper face has the hole for the guide shaft 2ac, in which the guide shaft 1 is inserted movably. This hole 2ac is provided at the front side wall part 2aa, in which the projecting plate 2aab having the projected release plate supporting part 2aaa on the rear face is upwardly projected to the rear side wall part 2ab. Further, the block part 2a is freely moved in the axial direction in a slide block moving chamber 3c of the housing 3 described below. Further, the projecting plate 2aab of the block part 2a can be directly operated by a finger or the like from the upper side of the slide block moving chamber 3c, and is formed so as to be projected from the upper part of the slide block moving chamber 3c, as illustrated in FIG. 1 or 2. So, the operativity is sufficient.

The block part 2a has the rod-like piston shafts 2b, 2b, which are projected at the position on the both sides of the hole for the guide shaft 2ac of the front side wall part 2aa, and are in approximately parallel to the center axis of the hole for the guide shaft 2ac. As for the one pair of the piston shafts 2b, 2b, when the block part 2a is moved in the front direction in the axial direction in the slide block moving chamber 3c described below, the piston shafts 2b, 2b are respectively slid in the front direction in a piston shaft guide passages 3d, 3d. Then, the front end sides of the shafts 2b, 2b are projected from the cartridge mounting part 3a side of the piston shaft guide passages 3d, 3d, and pressed the cap for pushing out the stored material of the cartridge in the front direction. As for the one pair of the piston shafts 2b, 2b, although the shafts may have a circle or non-circle shaped cross section, it is desired at least that the shafts have shapes capable of respectively sliding in the piston shaft guide passages 3d, 3d, and have shapes corresponding to the cross sections of the piston shaft guide passages 3d, 3d.

In the space between the front side wall part 2aa and the rear side wall part 2ab of the block part 2a, as illustrated in FIGS. 1 to 3, there are the release plate 2c provided with the engaging hole for the guide 2ca, and the release plate pressing spring 2d for pressing the release plate 2c in the front direction. The engaging hole 2ca is formed to have a longer distance from the upper end to the lower end of the engaging hole 2ca than the diameter of the portion between the first stopper ring engaging groove 1c and the rotation knob mounting part 1e of the guide shaft 1. Further, the release plate 2c and the release plate pressing spring 2d are provided so as to have the states that the portion between the first stopper ring engaging groove 1c and the rotation knob mounting part 1e of the guide shaft 1 is inserted into the engaging hole for the guide 2ca, and the upper front face of the release plate 2c is contacted with the rear face of the release plate supporting part 2aaa of the projecting plate 2aab and that the upper end and the lower end of the engaging hole for the guide 2ca are contacted with the guide shaft 1. Thus, moving of the slide block 2 in the axial direction with respect to the guide shaft 1 can be controlled.

That is, as illustrated in FIG. 1 or 2, since the engaging hole for the guide 2ca of the release plate 2c has the longer distance from the upper end to the lower end thereof than the diameter of the portion between the first stopper ring engaging groove 1c and the rotation knob mounting part 1e of the guide shaft 1, when the release plate 2c is inclined in the block part 2a by the pressing force of the release plate pressing spring 2d, the upper end and the lower end of the engaging hole for the guide 2ca are engaged with an outer periphery of the guide shaft 1, and moving of the slide block 2 in the axial direction with respect to the guide shaft 1 is controlled by frictional force. In this state, the front face of the upper part of the release plate 2c is positioned at the rear face of the release plate supporting part 2aaa of the projecting plate 2aab and the front face of the lower part of the release plate 2c is positioned on the front side from the rear face of the release plate supporting part 2aaa of the projecting plate 2aab. Further, when the state of inclining of the release plate 2c is transferred to the state that the release plate 2c is in approximately perpendicular to the axis of the guide shaft 1 by pinching the release plate 2c by fingers or the like or by pressing forward the rear face of the upper part of the release plate 2c, the engaging of the upper end and the lower end of the engaging hole for the guide 2ca with respect to the outer periphery of the guide shaft 1 is separated. Thereby, the slide block 2 becomes in the state of being movable in the axial direction with respect to the guide shaft 1.

Reference numeral 3 is a housing comprising a cartridge mounting part 3a, a guide member pressing chamber 3b, a slide block moving chamber 3c, one pair of piston shaft guiding passages 3d, 3d, one pair of piston shaft pressing spring chambers 3e, 3e, and a lever mounting part 3f. The cartridge mounting part 3a is for mounting the cartridge storing the dental viscous material and provided at a front end of the housing 3. The guide member pressing chamber 3b has a guide member supporting part 3ba, a first guide shaft supporting part 3bb and a space 3bc. The guide member supporting part 3ba is for constantly supporting the cylindrical part 1ba of the guide member 1b and formed at a rear side of the cartridge mounting part 3a, where the cylindrical part 1ba is supported rotatably and silidably in the axial direction. The first guide shaft supporting part 3bb supports the portion between the first stopper ring engaging groove 1c and the rotation knob mounting part 1e, where the portion is supported rotatably and silidably in the axial direction. The space 3bc is formed between the guide member supporting part 3ba and the first guide shaft supporting part 3bb, and has an opening upper part, where the guide part 1bb of the guide member 1b can be rotated and moved. The slide block moving chamber 3c has a second guide shaft supporting part 3ca provided at a rear end wall on the rear side of the first guide shaft supporting part 3bb. The second guide shaft supporting part 3ca supports a portion between the first stopper ring engaging groove 1c of the guide shaft 1 and the rotation knob mounting part 1e, and this portion is supported rotatably and slidably in the axial direction. The slide block moving chamber 3c has an upper part opening to approximately full length. The one pair of the piston shaft guide passages 3d, 3d are provided on the both sides of the guide member pressing chamber 3b, slidably supports the piston shafts 2b of the slide block 2 in the axial direction, and penetrates from the slide block moving chamber 3c to the cartridge mounting part 3a. The one pair of the piston shaft pressing spring chambers 3e, 3e have piston shaft pressing springs 3ea so as to contact one side ends of these springs 3ea with the piston shafts 2b, 2b in the both piston shaft guide passages 3d, 3d. The lever mounting part 3f is provided at the upper part of the guide member pressing chamber 3b. The housing 3 supports the guide shaft 1 provided with the slide block 2, where the guide shaft 1 is supported rotatably and slidably in the axial direction, and is for rotatably mounting the lever main body 4 described below.

The front end of the housing 3 has the cartridge mounting part 3a for mounting the cartridge storing the dental viscous material. As the cartridge mounting part 3a, it is not especially limited if it has a shape corresponding to the shape of the cartridge to be mounted. However, for example, as illustrated in FIGS. 1 to 3, 5 and 6, if the cartridge mounting part 3a has engaging parts formed to have a point symmetrical shape with respect to the axis of the guide shaft 1 when seeing it from the front face side, the cartridge can be mounted easily and certainly by rotating the cartridge while contacting the rear end face of the cartridge with the front end face of the housing 3, so that it is preferable. More particularly, in the cartridge mounting part 3a illustrated in FIGS. 1 to 3, 5 and 6, when the cartridge is rotated clockwisely from the state that the rear end of the cartridge is positioned between the both engaging parts of the front end while contacting the rear end of the cartridge with the front end face of the housing 3, the rear end face of the cartridge is ridden over the projected parts provided at the upper part on the right side and the lower part on the left side of the front end face of the housing 3 in FIG. 6, and the rear end of the cartridge is engaged with the engaging part to be mounted. Thus, a person carrying out an operation for mounting the cartridge can understand that the cartridge is certainly mounted on the cartridge mounting part 3a of the housing 3 by the feeling with fingers when the rear end face of the cartridge is ridden over the projected part. Therefore, an operation feeling is remarkably improved. Further, it can be prevented to damage the cartridge and the dispenser for the dental viscous material when carrying out the operation for discharging in the state that the cartridge is incompletely mounted. So, it is preferable. Further, even when the cartridge is rotated counterclockwisely against will at the time of removing the cap or the like mounted on the cartridge in the state that the cartridge is mounted on the cartridge mounting part 3a, the cartridge is not easily reversed by the projected part provided at the housing 3. Thus, it can be prevented that the cartridge is removed accidentally during the operation or the like, so that it is preferable. Further, in the cartridge mounting part 3a illustrated in FIGS. 1 to 3, 5 and 6, the engaging parts are formed extending to the right side of the lower part and the left side of the upper part on of the front end face of the housing 3 in FIG. 6. Thus, even when the cartridge is given the strong force more for rotating clockwisely in the state the cartridge is mounted on the cartridge mounting part 3a, a pipe part of the cartridge is contacted with the portion where the engaging parts are extended, to thereby prevent the rotation of the cartridge to remove the cartridge, so that it is preferable.

Further, as illustrated in FIGS. 1 to 3, the guide member pressing chamber 3b is provided on the rear side of the cartridge mounting part 3a. The guide member pressing chamber 3b has the guide member supporting part 3ba, the first guide shaft supporting part 3bb and the space 3bc. The guide member supporting part 3ba is formed at the rear side of the cartridge mounting part 3a, and this part 3ba is for constantly supporting the cylindrical part 1ba of the guide member 1b, where the cylindrical part 1ba is supported rotatably and silidably in the axial direction. The first guide shaft supporting part 3bb supports the portion between the first stopper ring engaging groove 1c and the rotation knob mounting part 1e, where this portion is supported rotatably and silidably in the axial direction. The space 3bc is formed between the guide member supporting part 3ba and the first guide shaft supporting part 3bb, and has the opening upper part, where the guide part 1bb of the guide member 1b can be rotated and moved. Further, the slide block moving chamber 3c is provided at the rear side of the guide member pressing chamber 3b. The slide block moving chamber 3c has the second guide shaft supporting part 3ca formed at the rear end wall of the chamber 3c, at the rear side of the first guide shaft supporting part 3bb, and has the upper part opening to approximately full length. The second guide shaft supporting part 3ca supports the portion between the first stopper ring engaging groove 1c of the guide shaft 1 and the rotation knob mounting part 1e, and this portion is supported rotatably and slidably in the axial direction. Further, the guide shaft 1 is supported movably and slidably in the axial direction by the guide member supporting part 3ba, the first guide shaft supporting part 3bb and the second guide shaft supporting part 3ca. Further, as for the guide shaft, the possible moving distance in the axial direction is controlled by the space 3bc of the guide member pressing chamber 3b. Further, as for the slide block 2 mounted on the guide shaft 1, the possible moving distance in the axial direction is controlled by the slide block moving chamber 3c, and the operation for going back is carried out by pinching the release plate 2c and the projecting plate 2aab of the upper part of the slide block moving chamber 3c by fingers or the like.

As illustrated in FIGS. 1 to 3, the front side of the guide member supporting part 3*ba* has the guide shaft pressing spring 7 giving the force for constantly pressing the front end of the cylindrical part 1*ba* of the guide member 1*b* in the rear direction. Further, as for the guide shaft 1, the rear end side is constantly pressed in the rear direction by the spring 1*g* provided at the knob for rotating the guide shaft 1*h*, and the front end side is constantly pressed in the rear direction by the guide shaft pressing spring 7. Thus, the guide shaft 1 and the lever part 4*a* described below can be moved certainly, so that it is preferable. Further, it can be prevented to damage the guide member 1*b* or the housing 3 when the front end of the large diameter part 1*bba* fixed at the front end of the guide shaft 1 is violently crashed to the front end of the guide member pressing chamber 3*b*.

Further, the both sides of the guide member pressing chamber 3*b* have the one pair of the piston shaft guide passages 3*d*, 3*d* and the one pair of the piston shaft pressing spring chamber 3*e*, 3*e* respectively. The one pair of the piston shaft guide passages 3*d*, 3*d* support the piston shafts 2*b* at the slide block 2 where the piston shafts 2*b* are supported slidably in the axial direction, and penetrates from the slide block moving chamber 3*c* to the cartridge mounting part 3*a*, as illustrated in FIG. 3. The one pair of the piston shaft pressing spring chambers 3*e*, 3*e* have the piston shaft pressing springs 3*ea* so as to contact one side ends of these springs 3*ea* with the piston shafts 2*b*, 2*b* in the both piston shaft guide passages 3*d*, 3*d*, as illustrated in FIG. 4. As for the piston shaft guide passages 3*d*, 3*d*, when the rod-like piston shafts 2*b*, 2*b* are slid in the axial direction, the piston shaft guide passages 3*d*, 3*d* guide the piston shafts 2*b*, 2*b*, and control in order not to rotate the piston shafts 2*b*, 2*b* with respect to the axis of the guide shaft 1, where the shafts 2*b*, 2*b* are respectively projected on the both sides of the hole for the guide shaft 2*ac* of the front side wall part 2*aa* in the state that the axes of the shaft 2*b*, 2*b* are in approximately parallel to the center axis of the hole for the guide shaft 2*ac*. Further, the piston shaft pressing springs 3*ea*, 3*ea*, which are respectively provided at the piston shaft pressing spring chambers 3*e*, 3*e*, constantly give the pressing force to the piston shafts 2*b*, 2*b*, to thereby control in order not to move the piston shafts 2*b*, 2*b* in the axial direction even by the small force.

As illustrated in FIGS. 1 and 2, the upper part of the guide member pressing chamber 3*b* of the housing 3 has the lever mounting part 3*f*, and the space for mounting the lever main body 4. The space is formed for rotating the lever part 4*a* of the lever main body 4 described below at least from the position, which is in approximately parallel to the upper face of the housing 3, to the position where the rear part of the lever part 4*a* has the predetermined angle with respect to the upper face of the housing 3.

Reference numeral 4 is a lever main body, which comprises a lever part 4*a* and a pressing piece 4*b*. The lever part 4*a* is provided at the lever mounting part 3*f* of the housing 3, and axially supported by a lever shaft 4*aa* so as to be rotated from at least the position being approximately parallel to the upper face of the housing 3 to a position where a rear part thereof has a predetermined angle with respect to the upper face of the housing 3. The pressing piece 4*b* is projected at a lower part on the front end side of the lever part 4*a*. The lever pressing piece 4*b* is inserted into the small diameter part 1*bbb* of the guide part 1*bb* when it is in the initial position being approximately parallel in the upper face of the housing 3. The lever pressing piece 4*b* is moved to a rear part through a stepped part at a boundary between a small diameter part 1*bbb* and a large diameter part 1*bba* of the guide part 1*bb* by rotating the knob for rotating the guide shaft 1*h*. Then, the pressing piece 4*b* rotates the lever part 4*a* upwardly by predetermined angles, and is contacted with a rear face of the large diameter part 1*bba* of the guide part 1*bb*. Further, the pressing piece 4*b* moves the rear face of the large diameter 1*bba* of the guide part 1*bb* in the front direction when a rear end of the lever part 4*a* is pressed on the housing 3 side. When the lever main body 4 presses the guide member 1*b* of the guide shaft 1, the guide shaft 1 is moved in the front direction, and to thereby move the one pair of piston shafts 2*b*, 2*b* which are provided on the guide shaft 1. Then, the viscous material stored in the cartridge is discharged by pressing the cap for pushing out the stored material of the cartridge in the front direction, where the cartridge is mounted on the cartridge mounting part 3*a* of the housing 3.

The lever part 4*a* of the lever main body 4 is axially supported by the lever shaft 4*aa* so as to be rotated at least from the position being in approximately parallel to the upper face of the housing 3 as illustrated in FIG. 2 to the position where the rear part has the predetermined angle with respect to the upper face of the housing 3 as illustrated in FIG. 1. That is, when the knob for rotating the guide shaft 1*h* mounted on the rotation knob mounting part 1*e* formed at the rear end of the guide shaft is rotated, the large diameter part 1*bba* of the guide part 1*bb* of the guide member 1*b* is moved to upper side. The lever part 4*a* axially supported on the lever shaft 4*aa* is rotated by the pressing piece 4*b*, which is moved in the rear direction by the rear face of the large diameter part 1*bba*. Then, the lever part 4*a* is axially supported by the lever shaft 4*aa* so as to be rotated until it has the predetermined angle with respect to the upper face of the housing 3. The lever part 4*a* has the constitution capable of positioning at the initial position being in approximately parallel to the upper face of the housing 3. Thus, since the lever does not become obstructive at the time of keeping the dispenser, the keeping space can be remarkably decreased as compared with the conventional dispenser for the dental viscous material.

Further, the lever part 4*a* of the lever main body 4 has a stopper 5 provided movably, where the stopper 5 has a projected part 5*a* projected downwardly, as illustrated in FIGS. 1, 2, 4 and 5. Further, a recessed part 3*g* is formed at a position corresponding to the projected part 5*a* on the upper face side of the housing 3 when the stopper 5 is positioned on the most rear side. Then, the rotation angle of the lever part 4*a* can be controlled by moving the stopper 5 in the frontward and rearward directions. Therefore, when the rear end of the lever part 4*a* is pressed on the housing 3 side, the strokes of the piston shafts 2*b*, 2*b* can be adjusted. Thus, the discharging amount of the viscous material can be changed, so that it is preferable. Further, in the case that the dispenser for the dental viscous material according to the present invention is kept, when the stopper 5 is moved to the position on the most rear side, the projected part 5*a* of the stopper 5 can be inserted into the recessed part 3*g* on the upper face of the housing 3, to thereby take the position being in approximately parallel to the upper face of the housing 3, as illustrated in FIG. 4. Thus, the space for keeping the dispenser can be decreased, so that it is preferable.

Further, as illustrated in FIG. 2, the lever part 4*a* of the lever main body 4 is formed to have a U-shaped cross section where the lower part is opened, and this part is formed so as to cover the projecting plate 2*aab* of the slide block 2 and the release plate 2*c*, where the projecting plate 2*aab* is projected from the slide block moving chamber 3*c*. Then, when the dispenser for the dental viscous material according to the present invention is kept, it is more miniaturized. So, it is preferable. Further, when the lever part 4c takes the initial position being in approximately parallel to the upper face of the housing 3, the slide block moving chamber 3c is covered by the lever part 4a. Thus, when the dispenser is kept, it can be prevented that dust, extraneous substance or the like is invaded into the housing 3 to damage the operativity of the dispenser or the dispenser itself. So, it is preferable. Further, since the inside of the housing 3 cannot be seen from the outside, it gives better appearance, so that it is preferable. Further, as illustrated in FIGS. 1 and 2, if the lever part 4a of the lever main body 4 can be rotated from the initial position being in parallel to the guide shaft to the position being in approximately perpendicular to the guide shaft 1, the dispenser can be more miniaturized as compared with the dispenser at the time of using it, when the dispenser for the dental viscous material according to the present invention is kept. So, it is preferable. Further, an operation for holding the projecting plate 2aab of the slide block 2 and the release plate 2c can be easily carried out, so that it is preferable.

The pressing piece 4b is projected at the lower part on the front end side of the lever part 4a. When the lever part 4a is inserted into the small diameter part 1bbb of the guide part 1bb in the initial position being in approximately parallel to the upper face of the housing 3 as illustrated in FIG. 2 and the knob for rotating the guide shaft 1h is rotated, the pressing piece 4b is moved in the rear direction by the stepped part of the boundary between the small diameter part 1bbb and the large diameter part 1bba as illustrated in FIG. 1. Then, the pressing piece 4b upwardly rotates the lever part 4a by the predetermined angle and is contacted with the rear face of the large diameter part 1bba of the guide part 1bb. Further, when the rear end of the lever part 4a is pressed on the housing 3 side, the pressing piece 4b moves the rear face of the large diameter part 1bba in the front direction. As illustrated in FIG. 2, the pressing piece 4b is inserted into the small diameter part 1bbb in the state that the small diameter part 1bbb of the guide part 1bb is directed upwardly. Thus, the lever part 4a can be freely rotated from the initial position being in approximately parallel to the upper face of the housing 3 to the position where the rear part thereof has the predetermined angle with respect to the upper face of the housing 3. Further, when the lever part 4a is rotated to be transferred to the position being in approximately parallel to the upper face of the housing 3, the dispenser becomes in the discharge release state where the guide shaft 1 cannot be transferred in the front direction.

On the other hand, when the knob for rotating the guide shaft 1h is rotated to transfer from the state where the small diameter part 1bbb of the guide part 1bb is directed upwardly as illustrated in FIG. 2 to the state where the large diameter part 1bba of the guide part 1bb is directed upwardly as illustrated in FIG. 1, the pressing piece 4b is moved in the rear direction by the stepped part of the boundary between the small diameter part 1bbb and the large diameter part 1bba as illustrated in FIGS. 8 to 11. Thus, the lever part 4a is rotated from the initial position being in approximately parallel to the upper face of the housing 3 to the position where the rear part thereof has the predetermined angle with respect to the upper face of the housing 3. Further, the pressing piece 4b is moved to the rear face of the large diameter part 1bba to have the discharge possible state. Thus, when the rear end of the lever part 4a is pressed on the housing 3 side in such the state, the pressing piece 4b presses the rear face of the large diameter part 1bba to move the guide shaft 1 in the front direction.

Then, a method for using the dispenser for the dental viscous material according to the present invention, which has the above-described constitutions, is explained.

First, as a preparation, an operation for mounting the cartridge storing the dental viscous material on the cartridge mounting part 3a of the dispenser for the dental viscous material according to the present invention is carried out. This operation is carried out as follows. When the piston shafts 2b, 2b are projected from the cartridge mounting part 3a as illustrated in FIGS. 1 to 5, the cartridge cannot be mounted since the piston shafts 2b, 2b become obstructive. Thus, the lever part 4a is rotated upwardly at first, and the release plate 2c and the projecting plate 2aab at the upper part of the slide block moving chamber 3c are held by fingers or the like, to thereby transfer the state that the release plate 2c is inclined to the state the release plate 2c is approximately vertical to the center of the guide shaft 1. Then, engagement of the upper end and the lower end of the engaging hole for the guide 2ca with the outer periphery of the guide shaft 1 is released. Further, while keeping the engagement release state, that is, while keeping the state the release plate 2c and the projecting plate 2aab are held by the fingers or the like, the block part 2a is moved in the rear direction until having the state that the piston shafts 2b, 2b are not projected from the cartridge mounting part 3a. After that, the cartridge is mounted on the cartridge mounting part 3a.

Then, the following operation is carried out. It is an operation comprising, pressing the upper part of the rear face of the release plate 2c in the front direction, transferring to the state that the release plate 2c is approximately vertical to the axis of the guide shaft 1, releasing the engaging of the upper end and the lower end of the engaging hole for the guide 2ca with respect to the outer periphery of the guide shaft 1, pressing the upper part of the rear face of the release plate 2c in the front direction, and thereby moving the block part 2a in the front direction until the top ends of the piston shafts 2b, 2b are contacted with the viscous material pushing out member of the cartridge, which is mounted on the cartridge mounting part 3a. This operation may be carried out according to the necessity. For example, this operation is carried out in a case that when there are little mounts of the viscous materials in the cartridge, the top ends of the piston shafts 2b, 2b can not be contacted with the viscous material pushing out members of the cartridge unless pressing of the rear end of the lever part 4a on the housing 3 side is repeated, (that is, a case that an idle striking is needed repeatedly), or a case that the viscous materials stored in the cartridge should be to discharged immediately by pressing the rear end of the lever part 4a on the housing 3 side as described below.

Then, when the dispenser for the dental viscous material according to the present invention is in the discharge release state, an operation for changing from the discharge release state to the discharge possible state is carried out by rotating the knob for rotating the guide shaft 1h.

At this time, when the knob for rotating the guide shaft 1h is rotated, the state where the small diameter part 1bbb of the guide part 1bb is directed upwardly as illustrated in FIG. 2 is transferred to the state where the large diameter part 1bba of the guide part 1bb is directed upwardly as illustrated in FIG. 1. Thus, the pressing piece 4b of the lever main body 4, which is inserted in the small diameter part 1bbb, is moved in the rear direction by the stepped part of the boundary between the small diameter part 1bbb and the large diameter part 1bba of the guide part 1bb, as illustrated in FIGS. 8 to 11. Then, the pressing piece 4b rotates the lever part 4a from the initial position being in approximately parallel to the upper face of the housing 3 to the position where the rear part of the lever part 4 has the predetermined angle with respect to the upper face of the housing 3. Further, the pressing piece 4b is moved to the rear face of the large diameter part 1bba of the guide part 1bb. Thus, the discharge release state can be changed to the discharge possible state. In the discharge release state, the guide shaft 1 cannot be moved in the front direction even when the lever part 4a is rotated to be transferred to the position being in approximately parallel to the upper face of the housing 3. In the discharge possible state, when the rear end of the lever part 4a is pressed to the housing 3 side, the pressing force is transmitted to the guide shaft 1, to thereby move the guide shaft 1 in the front direction.

After finishing such the preparation, an operation for discharging desired amount of the dental viscous material from the inside of the cartridge mounted on the cartridge mounting part 3a of the dispenser for the dental viscous material according to the present invention is carried out.

This operation is carried out until the desired amount of the dental viscous material is discharged by repeating the following two steps in orders. The operation comprises the steps for pressing the rear end of the lever part 4a, which is rotated until the rear part thereof has the predetermined angle with respect to the upper face of the housing 3, and rotating the lever part 4a again until the rear part thereof has the predetermined angle with respect to the upper face of the housing 3 by releasing the pressing to the lever part 4a.

At this time, when the rear end of the lever part 4a is pressed on the housing 3 side against the pressing force by the spring 1g in the knob for rotating the guide shaft 1h or the guide shaft pressing spring 7, the lever part 4a is rotated around the lever shaft 4aa as a supporting point. Then, the pressing piece 4b projected at the lower part on the front end side of the lever part 4a presses the rear face of the large diameter part 1bba of the guide part 1bb in the front direction. Further, the pressing piece 4b moves the guide shaft 1 and the one pair of the piston shafts 2b, 2b in the front direction, where the one pair of the piston shafts 2b, 2b are projected at the slide block 2, which is integrated with the guide shaft 1 by the frictional force of the release plate 2c. Then, the top ends of the piston shafts 2b, 2b press the viscous material pushing out member of the cartridge, to thereby discharge the dental viscous material from the inside of the cartridge.

That is, the release plate 2c of the slide block 2 is inclined in the block part 2a by the pressing force of the release plate pressing spring 2d, where the front face of the upper part is positioned at the rear face of the release plate supporting part 2aaa of the projecting plate 2aab, and the front face of the lower part is positioned on the front side from the rear face of the release plate supporting part 2aaa of the projecting plate 2aab. When the release plate 2c is so inclined, the upper end and the lower end of the engaging hole for the guide 2ca of the release plate 2c are engaged with the outer periphery of the guide shaft 1, to thereby control moving of the slide block 2 in the axial direction with respect to the guide shaft 1 by the frictional force. However, when the guide shaft 1 is moved in the front direction in the state that the release plate 2c is inclined with respect to the axis of the guide shaft 1, the force is added to the guide shaft 1 for moving the lower part of the release plate 2c more in the front direction. Further, as the inclining of the release plate 2c is increased, the upper end and the lower end of the engaging hole for the guide 2ca of the release plate 2c has more stronger pressing force, which is given to the outer periphery of the guide shaft 1, to thereby remarkably increase the frictional force. Thus, the slide block 2 is integrated with the guide shaft to be moved in the front direction against the piston shaft pressing springs 3ea, 3ea, which directly give the pressing force to the one pair of the piton shafts 2b, 2b.

On the other hand, when pressing to the lever part 4a is released, the guide shaft 1 is moved in the rear direction by the pressing forces of the spring 1g of the knob for rotating the guide shaft 1h and the guide shaft pressing spring 7. Further, the pressing piece 4b of the lever part 4a is pressed in the rear direction by the rear face of the large diameter part 1bba of the guide part 1bb of the guide member 1b fixed to the guide shaft 1, and the lever part 4a is rotated upwardly by the predetermined angle around the lever shaft 4aa as the supporting point, and is returned to the initial position. However, the slide block 2 is not moved in the rear direction like the guide shaft 1 by the piston shaft pressing springs 3ea, 3ea, which directly give the pressing force to the piston shafts 2b, 2b, so that the slide block 2 keeps the state of being moved in the front direction. Thus, the front ends of the piston shafts 2b, 2b are respectively contacted with the viscous material pushing out members of the cartridge, so that these shafts 2b, 2b become ready for next pushing immediately.

That is, the release plate 2c in the slide block 2 is inclined as described above, and the upper end and the lower end of the engaging hole for the guide 2ca of the release plate 2c are engaged with the outer periphery of the guide shaft 1, to thereby control moving of the slide block 2 in the axial direction with respect to the guide shaft 1 by the frictional force. However, when the guide shaft 1 is moved in the rear direction in the state that the release plate 2c is inclined with respect to the axis of the guide shaft 1, the guide shaft 1 is added the force for moving the lower part of the release plate 2c in the rear direction, so that the release plate 2c is transferred to the direction of being perpendicular to the axis of the guide shaft 1. Thus, the pressing force of the upper end and the lower end of the engaging hole for the guide 2ca of the release plate 2c to the outer periphery of the guide shaft 1 is decreased. Thereby, the frictional force is more decreased as compared with the state that the slide block 2 is stopped with respect to the guide shaft 1. As the result of this, the guide shaft 1 is moved in the rear direction. However, the slide block 2 is not moved in the rear direction like the guide shaft 1 by the piston shaft pressing springs 3ea, 3ea, which directly give the pressing force to the piston shafts 2b, 2b, so that the slide block 2 keeps the state of being moved in the front direction.

The operation for pressing the rear end of the lever part 4a to the housing 3 side and the operation for releasing the pressing to the lever part 4a are repeated, to thereby move the guide shaft 1 frontward and rearward in that way. Then, these operations may be carried out until obtaining the desired amount of the dental viscous material by intermittently moving the slide block 2 in the slide block moving chamber 3c by working of the release plate 2c and the piston shaft pressing springs 3ea, 3ea, pressing the viscous material pushing out members of the cartridge by the piston shafts 2b, 2b, and successively discharging the dental viscous material from the inside of the cartridge.

After obtaining the desired amount of the dental viscous material in that way, when the dispenser for the dental viscous material according to the present invention is desired to be put on the work table or kept in the refrigerator or the rack, in the states that the cartridge having the remained viscous material is mounted on the cartridge mounting part 3a and the top end of the piston shaft 2b is contacted with the viscous material pushing out member of the cartridge. The operation for changing from the discharge possible state to the discharge release state can be carried out by rotating the knob for rotating the guide shaft 1h. In such a state, although the lever part 4a of the lever main body 4 can be freely rotated from the initial position being in approximately parallel to the upper face of the housing 3 to the position where the rear part thereof has the predetermined angle with respect to the upper face of the housing 3, the viscous material stored in the cartridge mounted on the cartridge mounting part 3a cannot be discharged. Thus, even when the lever part 4a of the lever main body 4 is rotated to be transferred to the position being in approximately parallel to the upper face of the housing 3, the trouble that the viscous material stored in the cartridge is discharged against will is not generated at all. Further, since the lever part 4a can be positioned at the initial position being in approximately parallel to the upper face of the housing 3, the lever does not become obstructive when the dispenser is kept. Thus, the keeping space of the dispenser can be remarkably decreased as compared with that of the conventional dispenser for the dental viscous material.

At this time, when the knob for rotating the guide shaft 1h is rotated, the state that the large diameter part 1bba of the guide part 1bb of the guide member 1b is directed upwardly as illustrated in FIG. 1 is transferred to the state that the small diameter part 1bbb of the guide part 1bb of the guide member 1b is directed upwardly as illustrated in FIG. 2. Thus, the pressing piece 4b of the lever main body 4 in the state of being contacted with the rear face of the large diameter part 1bba of the guide part 1bb is moved again in the front direction by the stepped part of the boundary between the small diameter part 1bbb and the large diameter part 1bba of the guide part 1bb as illustrated in FIGS. 8 to 11. Then, the pressing piece 4b is returned to the state of being inserted into the small diameter part 1bbb of the guide part 1bb. Thus, the discharge possible state is changed to the discharge release state. In the discharge possible state, when the rear end of the lever part 4a is pressed to the housing 3 side, the pressing force is transmitted to the guide shaft 1, to thereby transfer the guide shaft 1 in the front direction. In the discharge release state, the guide shaft 1 cannot be moved in the front direction even when the lever part 4a is rotated to be transferred to the position being in approximately parallel to the upper face of the housing 3.

Further, when the dispenser for the dental viscous material according to the present invention is used again, after the dispenser is put on the work table or kept in the refrigerator or the rack, in the states that the cartridge having the remained viscous material is mounted on the cartridge mounting part 3a, where the top end of the piston shaft 2b is contacted with the viscous material pushing out member of the cartridge, only by rotating the knob for rotating the guide shaft 1h to thereby change from the discharge release state to the discharge possible state, the viscous material stored in the cartridge can be discharged immediately.

Finally, when the cartridge is removed from the dispenser for the dental viscous material according to the present invention, this cartridge may be removed by the steps of upwardly rotating the lever part 4a; holding the release plate 2c and the projecting plate 2aab from the upper direction of the slide block moving chamber 3c by fingers or the like; transferring the state that the release plate 2c is inclined to the state that the release plate 2c is approximately perpendicular to the axis of the guide shaft 1; releasing the engaging of the upper end and the lower end of the engaging hole for the guide 2ca with respect to the outer periphery of the guide shaft 1; moving the block part 2a in the rear direction until having the state that the piston shafts 2b, 2b are not projected to the cartridge mounting part 3a while keeping the state that the engaging is released, that is, holding the release plate 2c and the projecting plate 2aab by fingers or the like; and thereafter removing the cartridge from the cartridge mounting part 3a.

What is claimed is:

1. A dispenser for a dental viscous material comprising, a guide shaft comprising a guide member mounting part, a guide member, a first stopper ring engaging groove, a first stopper ring, a rotation knob mounting part, a second stopper ring, a spring, and a knob for rotating the guide shaft, wherein the guide member has a cylindrical part at a front side of the guide member mounting part formed at a front end of the guide shaft, and a guide part at a rear side of the guide member mounting part, in which the guide part comprises a large diameter part and a small diameter part increasing its diameter toward a rear side, wherein the first stopper ring is engaged with the first stopper ring engaging groove, which is formed at the rear side of the guide member mounting part, wherein the second stopper ring is engaged with the second stopper ring engaging groove of the rotation knob mounting part, which is formed at a rear end of the guide shaft, wherein the knob for rotating the guide shaft is freely fit to a non-circle part formed at a rear side of the second stopper ring engaging groove, and is constantly given the force for sliding in the front direction of the shaft by a spring, which is provided at a space between the second stopper ring and a rear end part of the knob, and wherein at least a portion between the rear side of the first stopper ring engaging groove and the front side of the rotation knob mounting part has a pillar shape, said dispenser also comprising, a slide block comprising a box-shaped block part, rod-like piston shafts, a release plate, and a release plate pressing spring, wherein the box shaped slide block part has a hole for the guide shaft being provided at a front side wall part and a rear side wall part, in which the guide shaft is inserted movably in this hole for the guide shaft and a projecting plate having a projected release plate supporting part on a rear face is upwardly projected from the front side wall part, and further at least an opening upper face, wherein the rod-like piston shafts are projected at positions on the both sides of the hole for the guide shaft of the front side wall part of the box-shaped block part, in the state that the axes of the shafts are in approximately parallel to a center axis of the hole for the guide shaft, wherein the release plate has an engaging hole for the guide in the space of the block part, in which the portion between the first stopper ring engaging groove of the guide shaft and the rotation knob mounting part is inserted in the engaging hole for the guide, and a distance from the upper end to the lower end of the engaging hole for the guide is longer than the diameter of this portion, and further, the release plate has the front face contacted with the rear face of the release plate supporting part of the projecting plate at the upper part thereof, and wherein the release plate pressing spring presses the release plate in the front direction so as to contact the upper end and the lower end of the engaging hole for the guide with the guide shaft in the space of the block part, said dispenser also comprising, a housing comprising a cartridge mounting part, a guide member pressing chamber, a slide block moving chamber, one pair of piston shaft guiding passages one pair of piston shaft pressing spring chambers and a lever mounting part, wherein the cartridge mounting part is provided at a front end of the housing, and this part is for mounting the cartridge storing the dental viscous material, wherein the guide member pressing chamber has a guide member supporting part, a first guide shaft supporting part and a space, wherein the guide member supporting part is formed at a rear side of the cartridge mounting part and is for constantly supporting the cylindrical part of the guide member, where the cylindrical part is supported rotatably and silidably in the axial direction, wherein the first guide shaft supporting part supports the portion between the first stopper ring engaging groove of the guide shaft and the rotation knob mounting part, where the portion is supported rotatably and silidably in the axial direction, wherein the space is formed between the guide member supporting part and the first guide shaft supporting part, and has an opening upper part, where the guide part of the guide member can be rotated and moved, wherein the slide block moving chamber has a second guide shaft supporting part at a rear end wall of the chamber, where the second guide shaft supporting part is at a rear part of the first guide shaft supporting part, and has an upper part opening to approximately full length, where the second guide shaft supporting part supports a portion between the first stopper ring engaging groove of the guide shaft and the rotation knob mounting part, and this portion is supported rotatably and slidably in the axial direction, wherein the one pair of the piston shaft guide passages is provided on the both sides of the guide member pressing chamber, slidably supports the piston shaft of the slide block in the axial direction, and penetrates from the slide block moving chamber to the cartridge mounting part, wherein one pair of the piston shaft pressing spring chambers has piston shaft pressing springs so as to contact one side ends of these springs with the piston shafts in the both piston shaft guide passages and wherein the lever mounting part is provided at the upper part of the guide member pressing chamber, and said dispenser also comprising, a lever main body comprising a lever part and a pressing piece, wherein the lever part is provided at the lever mounting part of the housing and axially supported by a lever shaft so as to be rotated at least from the position being approximately parallel to the upper face of the housing to a position where a rear part thereof has a predetermined angle with respect to the upper face of the housing, and wherein the pressing piece is projected at a lower part on the front end side of the lever part, inserted into the small diameter part at the initial position being in approximately parallel to the upper face of the housing, moved in a rear direction by a stepped part at a boundary between a small diameter part and a large diameter part of the guide part when the knob for rotating the guide shaft is rotated, rotates the lever part upwardly by the predetermined angles, is contacted with a rear face of the large diameter part of the guide part, and moves the rear face of the large diameter part in the front direction when a rear end of the lever part is pressed on the housing side.

2. The dispenser for the dental viscous material as claimed in claim 1,
wherein the lever part of the lever main body has a stopper having a projected part projected downwardly, the stopper is provided movably, and a recessed part is formed at a position corresponding to the projected part on the upper face side of the housing when the stopper positions on the most rear side.

3. The dispenser for the dental viscous material as claimed in claim 2,
wherein the lever part of the lever main body is positioned at an initial position being an parallel to the guide shaft, and can be rotated from the initial position to a position being approximately perpendicular to the guide shaft.

4. The dispenser for the dental viscous material as claimed in claim 1,
wherein the lever part of the lever main body is formed to have a U-shaped cross section having an opening lower part so as to cover the projecting plate and the release plate of the slide block, where the projecting plate and the release plate are projected from the slide block moving chamber of the housing.

5. The dispenser for the dental viscous material as claimed in claim 1,
wherein a front face of the knob for rotating the guide shaft and a rear end outer face of the housing have a projected part and a recessed part, and these parts and are engaged each other when the guide part is rotated to the predetermined position by the knob for rotating the guide shaft.

6. The dispenser for the dental viscous material as claimed in claim 2,
wherein the lever part of the lever main body is formed to have a U-shaped cross section having an opening lower part so as to cover the projecting plate and the release plate of the slide block, where the projecting plate and the release plate are projected from the slide block moving chamber of the housing.

7. The dispenser for the dental viscous material as claimed in claim 2,
wherein a front face of the knob for rotating the guide shaft and a rear end outer face of the housing have a projected part and a recessed part, and these parts and are engaged each other when the guide part is rotated to the predetermined position by the knob for rotating the guide shaft.

8. The dispenser for the dental viscous material as claimed in claim 1,
wherein the lever part of the lever main body is positioned at an initial position being an parallel to the guide shaft, and can be rotated from the initial position to a position being approximately perpendicular to the guide shaft.

9. The dispenser for the dental viscous material as claimed in claim 1,
wherein a guide shaft pressing spring is provided on the front side of the guide member supporting part of the housing, where the spring is for constantly giving pressing force to a front end of the cylindrical part of the guide member in the rear direction.

* * * * *